United States Patent
Haggiag (12)

(10) Patent No.: US 11,344,252 B2
(45) Date of Patent: May 31, 2022

(54) INTRAORAL DEVICE FOR CREATING A SENSATION OF CONTACT, METHOD FOR APPLYING AN INTRAORAL DEVICE, AND METHOD FOR DETERMINING THE THICKNESS OF AN INTRAORAL DEVICE

(71) Applicant: Alain Haggiag, Sao Paulo (BR)

(72) Inventor: Alain Haggiag, Sao Paulo (BR)

( * ) Notice: Subject to any disclaimer, the term of this patent is extended or adjusted under 35 U.S.C. 154(b) by 552 days.

(21) Appl. No.: 16/340,301

(22) PCT Filed: Jul. 28, 2017

(86) PCT No.: PCT/BR2017/050214
§ 371 (c)(1),
(2) Date: Apr. 8, 2019

(87) PCT Pub. No.: WO2018/076088
PCT Pub. Date: May 3, 2018

(65) Prior Publication Data
US 2020/0037951 A1 Feb. 6, 2020

(30) Foreign Application Priority Data
Oct. 28, 2016 (BR) .......................... 102016025357-8

(51) Int. Cl.
*A61B 5/00* (2006.01)
*A61F 5/56* (2006.01)
*A61B 5/389* (2021.01)

(52) U.S. Cl.
CPC ............ *A61B 5/4557* (2013.01); *A61B 5/389* (2021.01); *A61B 5/742* (2013.01); *A61B 5/7415* (2013.01);
(Continued)

(58) Field of Classification Search
CPC ..... A61B 5/4557; A61B 5/389; A61B 5/7415; A61B 5/742; A61B 2562/0252;
(Continued)

(56) References Cited

U.S. PATENT DOCUMENTS 4,457,708 A * 7/1984 Dufour .................... A61C 7/00
433/6
4,519,386 A * 5/1985 Sullivan .................. A61C 5/007
128/859
(Continued)

FOREIGN PATENT DOCUMENTS

BR   PI0412167 A    3/2006
WO   2009013371 A1  1/2009
WO   2011060294 A2  5/2011

*Primary Examiner* — May A Abouelela
(74) *Attorney, Agent, or Firm* — Emerson, Thomson & Bennett, LLC; Roger D. Emerson; Peter R. Detorre

(57) ABSTRACT

This invention presents an intraoral device for generation of contact perception between teeth, the device being configured for application to the upper or lower dental arch of a user and comprising a contact means (20, 20') configured to be associated with at least a portion of one to four posterior teeth (D1) of the upper or lower dental arch, the device (10) being configured to generate a perception of contact to the user upon the contact between the contact means (20, 20') and at least a portion of the opposing arch to at least a portion of one to four posterior teeth (D1), offering the option of an accessible intraoral device for practical use to the user, and that does not impair the mouth functions of the user during its use in the waking period. This invention further comprises a method of applying the device which allows the user to apply the device without assistance of a skilled professional, and a method for determining the thickness of the aforesaid device.

18 Claims, 9 Drawing Sheets

Figure 1:
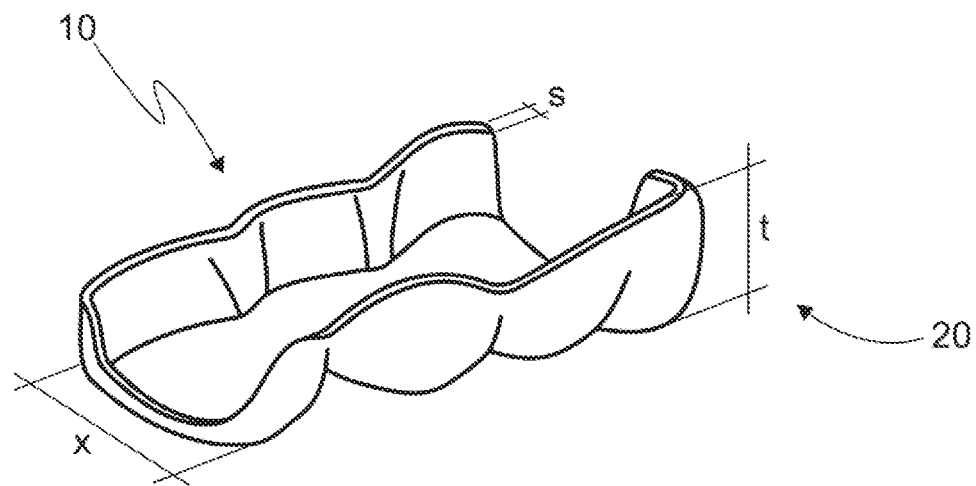

(52) U.S. Cl.
CPC ...... *A61F 5/566* (2013.01); *A61B 2562/0252* (2013.01); *A61F 2005/563* (2013.01)

(58) Field of Classification Search
CPC . A61B 5/746; A61B 5/682; A61B 2562/0247; A61B 5/0022; A61B 5/486; A61B 5/6843; A61B 5/228; A61F 5/566; A61F 2005/563; A61C 19/05; A61C 5/82; A61C 7/08; A61C 7/36; A61C 9/00; A61C 19/04; A61C 19/045
USPC .......................... 600/587, 590; 128/859, 861
See application file for complete search history.

(56) References Cited

U.S. PATENT DOCUMENTS

| | | | |
|---|---|---|---|
| 5,401,234 A | 3/1995 | Libem | |
| 5,836,761 A * | 11/1998 | Belvedere | A63B 71/085 433/6 |
| 5,865,619 A * | 2/1999 | Cross, III | A61F 5/566 433/6 |
| 6,200,133 B1 | 3/2001 | Kittelsen | |
| 6,237,601 B1 * | 5/2001 | Kittelsen | A61F 5/566 128/859 |
| 6,371,758 B1 * | 4/2002 | Kittelsen | A63B 71/085 128/861 |
| 6,491,036 B2 * | 12/2002 | Cook | A63B 71/085 128/859 |
| 6,553,996 B2 * | 4/2003 | Kittelsen | A63B 71/085 128/859 |
| 6,598,605 B1 * | 7/2003 | Kittelsen | A63B 71/085 128/859 |
| 6,691,710 B2 * | 2/2004 | Kittelsen | A63B 71/085 128/859 |
| 6,820,623 B2 * | 11/2004 | Cook | A61C 7/08 128/859 |
| 8,074,658 B2 * | 12/2011 | Kittelsen | A63B 71/085 128/861 |
| 8,104,324 B2 * | 1/2012 | Hennig | G01M 7/08 73/12.01 |
| 8,453,650 B1 * | 6/2013 | Frey | A61C 5/90 128/859 |
| 8,567,408 B2 * | 10/2013 | Roettger | A63B 71/085 128/861 |
| 8,739,599 B2 * | 6/2014 | Hennig | A61B 5/0053 73/12.01 |
| 8,925,554 B2 * | 1/2015 | Hackman | A63B 71/085 128/861 |
| 10,085,821 B2 * | 10/2018 | Frey | A61C 5/90 |
| 2002/0144686 A1 | 10/2002 | Cook | |
| 2004/0103905 A1 * | 6/2004 | Farrell | A63B 71/085 128/861 |
| 2005/0115571 A1 * | 6/2005 | Jacobs | A63B 71/085 128/859 |
| 2005/0284489 A1 * | 12/2005 | Ambis | A63B 71/085 128/859 |
| 2006/0219250 A1 * | 10/2006 | Farrell | B32B 27/08 128/859 |
| 2010/0086890 A1 * | 4/2010 | Kuo | A61C 7/08 433/6 |
| 2010/0129762 A1 * | 5/2010 | Mason | A61C 7/002 433/6 |
| 2011/0094522 A1 | 4/2011 | Weisflog | |
| 2014/0186793 A1 * | 7/2014 | Kurti, Jr. | A61B 5/0075 433/73 |
| 2014/0373852 A1 * | 12/2014 | Kline | A61F 5/566 128/861 |
| 2015/0004555 A1 * | 1/2015 | Frey | A61F 5/566 433/6 |
| 2015/0031994 A1 * | 1/2015 | Straatmann | A63B 71/085 600/427 |
| 2015/0250642 A1 * | 9/2015 | Miquel | A61C 7/36 128/848 |
| 2015/0360115 A1 * | 12/2015 | Moses | A61C 5/00 128/862 |
| 2017/0007363 A1 * | 1/2017 | Boronkay | G05B 19/042 |
| 2017/0007365 A1 * | 1/2017 | Kopelman | A61C 7/08 |
| 2017/0008333 A1 * | 1/2017 | Mason | B23K 26/362 |
| 2017/0014220 A1 * | 1/2017 | Gildener-Leapman | A61C 7/36 |
| 2017/0347956 A1 * | 12/2017 | Zegarelli | A61B 5/0836 |
| 2018/0110591 A1 * | 4/2018 | Sato | A61C 7/002 |
| 2018/0263806 A1 * | 9/2018 | Toussaint | A61F 5/566 |
| 2018/0279975 A1 * | 10/2018 | Dekel | A61B 6/032 |

* cited by examiner

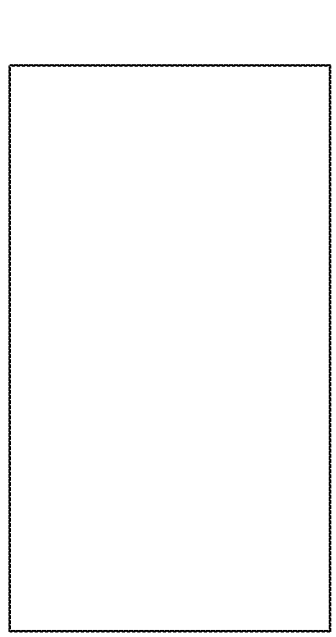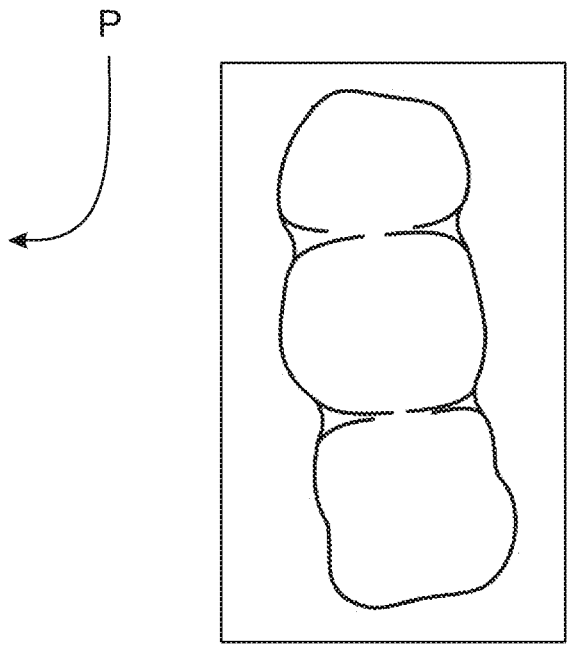
FIG.9A        FIG.9B
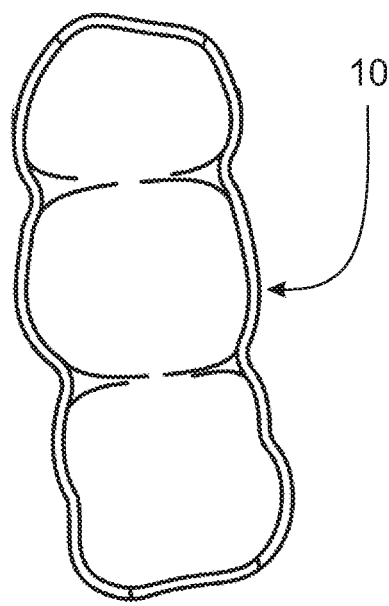
FIG.9C

INTRAORAL DEVICE FOR CREATING A SENSATION OF CONTACT, METHOD FOR APPLYING AN INTRAORAL DEVICE, AND METHOD FOR DETERMINING THE THICKNESS OF AN INTRAORAL DEVICE

This invention relates to an intraoral device for use during wakefulness (awake time) for the treatment of temporomandibular disorders (TMD), wherein said intraoral device helps the user to prevent the development of contractions of the masticatory and cervical muscles and the compression of the temporomandibular joints, aiming at the gradual reduction of parafunctions, that is, involuntary and/or unconscious disorders of movements such as bruxism, onychophagia, lip biting and other parafunctions performed during the patient's awake time.

In addition, this invention relates to a method for applying the aforementioned device.

This invention further relates to a method for determining the optimum thickness of the above-mentioned intraoral device according to the mouth anatomy of the user.

DESCRIPTION OF THE STATE OF THE ART

The temporomandibular joint—TMJ—is the structure that connects the jaw to the skull, being formed by bone tissues, articular disc, muscles, ligaments, joint capsule, among other structures, and having a dense blood and nerve supply.

Thus, temporomandibular disorders (TMD) consist of functional alterations associated with parafunctions such as muscular hyperactivity, trauma, emotional stress, bruxism, as well as numerous other factors that can lead to chronic headaches, neck pain, temporomandibular joint (TMJ) pain, orofacial pain, presence of articular and auditory noises such as tinnitus, limitation of jaw movements and irregular trajectory in the opening and closing movement of the mouth, dental, periodontal, prosthetic problems, among others.

For the treatment of temporomandibular disorders (TMDs), in many cases, a joint work is performed between a dental surgeon, a rheumatologist, a neurologist, an otolaryngologist, a speech therapist and a psychologist or psychiatrist.

According to epidemiological studies, 80 to 90% of the population (adults and children) have signs and symptoms of bruxism, but only 5% to 20% of these individuals are aware of this habit.

Bruxism can be mild and does not require treatment, however, it can be severe and intense and lead to joint and muscle disorders, headache, neck pain, ringing in the ears, dizziness, damage the teeth and even lead to their loss. It is common that people with nighttime bruxism only realize that they have this disorder when a more severe complication occurs (such as a fracture of a tooth) or when the person sleeping next to them complains of "grinding noises during sleep".

However, more recent studies (2013 to 2015) show that awake bruxism is more harmful than sleep bruxism and that it is the main risk factor for the appearance of myalgia and arthralgia associated to TMJ. In fact, these studies suggested that daytime clenching was nearly 6 times more frequent than sleep bruxism in patients with TMJ pain and masticatory muscle pain (especially in the temporal region).

Historically, a major part of the treatment is focused on the use of occlusal splints during the 'nighttime' period, especially for controlling the effects of this type of bruxism, such as tooth wear. These occlusal splints consist of removable intraoral devices, generally made of acrylic resin and designed to cover the incisal and occlusal surfaces of the teeth, in order to alter the occlusion of the patient, thus creating more adequate occlusal contacts and, temporarily, an orthopedically more stable articular position, in addition to promoting the protection of the teeth and offering support structures for abnormal forces that can wear or destroy them. It is known today that sleep splints do not treat sleep bruxism, but recent studies show a non-specific effect of this splint, at the level of the Central Nervous System, that may aid in the control of bruxism.

A conventional model found in the market consists of bite plates for nighttime use that only helps during the nighttime treatment, making it impossible to follow up on awake bruxism or 'daytime' bruxism, whose results show a direct association of cause and effect between the light dental tightness during wakefulness and pains in the sides of the head, that is, temporal and masseter muscles, in the TMJs and some tinnitus.

Above-mentioned daytime or awake bruxism can manifest itself in different ways, such as the constant clenching or touching of teeth or habits such as chewing gum or biting nails or lips, these being involuntary and unconscious behaviors.

A model of appliance for the treatment of awake or sleep bruxism is referred to as a device for incisal coverage, or 'Nociceptive Trigeminal Inhibition'—NTI, designed for the prevention of migraine, as well as for the prevention of the temporomandibular dysfunction. It comprises a small, shell-shaped and transparent appliance to be placed on the two front teeth; on the incisive edge of the appliance there is a protuberance or bar which extends itself to the front and to the back, setting a breakpoint.

Although the aforementioned state-of-the-art appliance can be used during daytime, it prevents any kind of communication between the user and other people during the use thereof, since it is of exclusive use in the upper central incisor teeth and has a protruding edge which makes contact with the lower incisor teeth.

Therefore, the user must use it in an absolute retracted way and, if they need to say something (in person or by phone), they should remove it for that purpose and, consequently, the treatment can be impaired.

There is also an app known in the market and called "Des-encoste-No Clenching", designed to be downloaded on mobile devices (smartphones, tablets or others) for 'Android' and 'iPhone' systems, whose objective is to, every hour or every other period defined by the user, issue sound signals or reminders that are completely customized by the user according to the instructions, for example, in that 'when teeth are not touching one can maintain the correct posture of the masticatory system', 'prevent muscle, dental, and periodontal overload', 'factors that can lead to facial pain/discomfort and dental problems', as well as offering a reminder for the user to use the nighttime splint.

The application has the "external" function of "reminding" the user to keep their teeth not touching, forcing them to adopt a new habit and to prevent the clenching of their teeth during daytime. Despite of the advantages offered by the appliance, such as the fact that it is free and easy to use, it has some disadvantages, such as in case of a signal issue, the application can be offline, thus reducing the effectiveness of the proposition.

Another drawback relates to the fact that some sound signals interfere with the sound signal of the app, and it may not be possible to differentiate them from other messages received, thus requiring the user to have to pick up the phone and read the message, and this requirement increases the level of stress of the user, a fact that aggravates bruxism.

Another drawback is that the app has a very restricted effectiveness, since it "catches the attention of the patient" every hour and does not "work" in real time.

As for tinnitus, which can also be a consequence of awake bruxism, until today it is treated with medication that improve blood circulation, with hyperbaric oxygen therapy having the patient in a pressurized chamber and breathing pure oxygen, with surgeries, control of the glycemic index, etc.

It turns out that said treatments by means of medications do not result in the improvement of all types of tinnitus, and they also do not identify the cause of the disorder, and, therefore, they are palliatives that do not allow the cure of the patient.

The state of the art anticipates the use of certain types of occlusal splints, such as the one disclosed in patent application No. PI 0605444-7 that consists of an occlusal splint for parafunction conditioning, including a device in the shape of the upper or lower dental arch, using the same parameter as used in dental impression trays, intended to condition patients with "bruxism syndrome", by means of the biofeedback technique, not to squeeze and/or grind their teeth during times of tension, and during sleep.

This device shown in document No. PI 0605444-7 is made of silicone or other durable material and is equipped with sensors, a control circuit, a power battery and vibrating motors designed to produce vibration that disturbs the user whenever they try to grind their teeth. Although effective in that it conditions the parafunction and prevents the tightening and grinding of teeth, the splint disclosed in PI 0605444-7 is intended for nighttime situations or for restricted social contact, since it is placed on all teeth of the upper or lower arch, which causes discomfort when eating, talking, or any other activity that uses the intraoral region, forcing the user to remove the splint in order to perform such activities. Furthermore, since it is placed along the entire length of the arch, the PI 0605444-7 splint creates an undesirable aesthetic aspect to the user, being easily seen by third parties and causing the mouth to appear unnatural. The same problem can be identified in patent application WO2011060294, which discloses a splint for application on the full extent of the lower or upper arch.

U.S. Pat. No. 5,911,576 relates to a measuring device to quantify the severity of bruxism, comprising a thin shell elastically retained by one or more teeth, of said casing, further comprising: a plurality of layers with mutually distinguishable colors, each color distinguishable from the adjacent layers; and a thickness of material which is larger than the previous one. When the outer layer of the casing is worn down by chewing, it reveals an inner layer. Frayed regions can be analyzed to determine the extent of bruxism. It is, therefore, a diagnostic device that does not have the function of generating a perception of contact to the user, nor of avoiding the occurrence of parafunctions.

In another patent, U.S. Pat. No. 4,838,283, an anti-bruxism device is presented (to be used during sleep). Said device uses the principle of bone conduction wherein sound vibrations from a sound generator are transmitted to a sound receiver when the user's jaw is closed/pressed against the opposing arch. The alarm develops a conditioned reflex in the user, and after a few alarms have gone off to alert about the occurrence of bruxism, the user no longer wakes up from sleep, but only reacts by relaxing the jaw when the alarm goes off. This device is specific for nighttime application, during rest and is not applicable to awake situations because it is not practical in this situation (it requires multiple electronic devices, impairing the movements and the use of the mouth, while also being unaesthetic for the user.

Patent document No. U.S. Pat. No. 3,813,781 relates to a bruxism monitoring device which comprises a flexible and inelastic nozzle having generally vertical side walls providing one or more recesses to accommodate one or more teeth and a thin interconnecting splint between the side walls for placement between upper and lower opposing teeth, and the splint includes a plurality of layers, each layer having a color that differentiates itself from the colors of the adjacent layers. It is, therefore, a diagnostic device that does not have the function of generating a perception of contact to the user, nor of preventing the occurrence of parafunctions. The same problem can be identified in patent application No. WO200913371, which discloses a splint for the diagnosis of bruxism, but not for its treatment, nor to generate a perception of contact to the user.

Other documents of the state of the art can be mentioned, which present problems that are fundamental to the proper use and to the intraoral aesthetics of the user. Patent application No. CN202096314, for example, deals with an intraoral device intended to provide biofeedback to the user in case of teeth grinding. The response to teeth grinding is given in the form of vibrations. In this case, the device is arranged to cover the full extent of the lower or upper arch, again impairing the functions and the aesthetics of the user's mouth. Additionally, the device is intended for nighttime application, and requires a control for its application, making it even more unfit for daytime use.

Patent application No. WO2014016641 discloses a vibration device for generating feedback to the user upon the touch of the opposing tooth in the device. In this case, the device has an integral electrical circuit inside it for vibration generation, which not only increases the perception of contact, but also significantly increases the size of the device, causing the above-mentioned practicality problems.

Furthermore, in addition to the problems already mentioned, all the above documents are relatively complex devices, obtained by manufacturing processes and whose application is quite specific, which makes it impossible to commercialize them on a large scale and makes it difficult for them to be used and understood by the ordinary user.

Therefore, an intraoral device for generating contact perception between said device and an opposing tooth, having a small construction, being practical and efficient for use, and whose procurement and application can be performed by an average user, is not observed in the state of the art.

OBJECTS OF THE INVENTION

A first object of this invention is to propose an intraoral device for generating contact perception that has a small size and ensures a practical and efficient use to the user.

A second object of this invention is to propose an intraoral device for generating contact perception whose application can be performed by an average user.

A third object of the present invention is to propose an intraoral device for generating contact perception that allows it to be used when the patient is awake, and which allows them to gradually correct the unwanted parafunctions by means of the response to the contact stimulus generated by the device A fourth object of this invention is to propose an intraoral device for the generation of contact perception that is reversible and non-invasive, allowing the user to perceive the positioning of the jaw in real time, ensuring that the user will experience a fast and conscious improvement.

BRIEF DESCRIPTION OF THE INVENTION

The objects of this invention are achieved through an intraoral device for generating perception of contact between teeth, the device being designed for application to the upper or lower dental arches of a user and comprising a contact means configured to be associated with at least a portion of one to four posterior teeth of the upper or lower dental arch.

Essentially, the device is configured to generate a perception of contact to the user upon contact between the contact means and at least a portion of the opposing arch to at least a portion of one to four posterior teeth.

Particularly, the contact means comprises a shape that covers the surface of at least a portion of one to four teeth, and the contact means is configured to adopt the shape of the surface of at least a portion of one to four teeth by pressing the contact means against at least a portion of one to four teeth to which it is associated.

The contact means comprises a state of malleability and a state of stiffness in at least a portion of its extent and configures the malleability state when subjected to a softening temperature range.

Moreover, at least a portion of the contact means is configured to, in the malleability state, assume the surface shape of at least a portion of one to four teeth upon its deformation by pressing the contact means against at least a portion of one to four teeth to which it is associated.

Particularly, the contact means is a splint whose thickness is at most the distance between the upper and lower arches of the user in a situation of minimal load on the user's jaw, and comprises a thickness between 0.5 and 10.0 mm.

More Particularly, the contact means comprises a thickness between 1.0 and 8.0 millimeters, 2.0 and 7.0 millimeters, or 2.0 and 4.5 millimeters.

In a possible configuration, the contact means is at least partially constituted of a metal filament.

In another possible configuration, the contact means comprises a rigid surface and a moldable surface, the moldable surface comprising the state of stiffness and the state of malleability. Optionally, the rigid surface is removable.

Furthermore, the contact means comprises, between the rigid surface and the moldable surface, a pressure sensor, the pressure sensor being connected to an application and being configured to send a signal to the application upon contact of the device with the opposing arch.

In another possible configuration, the device may comprise a pair of magnets disposed on the outer face of a pair of proximal teeth, the magnets being configured to send a signal to a receiving/transmitting unit upon the proximity between the magnets. The receiving/transmitting unit is configured to send information relating to the time and frequency of reception of the signals to an application on a mobile device.

This invention further comprises an alternative configuration of the intraoral device for generating contact perception between teeth, the device being configured for application to the upper or lower dental arch of a user and comprising a contact means configured to be associated with at least a portion of one to four posterior teeth of the upper or lower dental arch, the contact means comprising a thickness whose value is at most the distance between the user's upper and lower arches in a resting situation of the user's jaw.

In this regard, the contact means comprises a state of malleability and a state of stiffness in at least a portion of its extent, at least a portion of the extent of the contact means being configured to, in the malleability state, adopt the shape of the surface of at least a portion of one to four teeth by its deformation upon pressing the contact means against at least a portion of one to four teeth to which it is associated, the device being configured to generate a perception of contact to the user by means of the contact between the contact means and at least a portion of the opposing arch to at least a portion of a to four posterior teeth.

For this configuration, the contact means comprises a rigid surface and a moldable surface, the moldable surface comprising the state of stiffness and the state of malleability, and the rigid surface is removable. Furthermore, the contact means comprises, between the rigid surface and the moldable surface, a pressure sensor, the pressure sensor being connected to an application and being configured to send a signal to the application upon contact of the device with at least a portion of the opposing arch.

Still for this configuration, the device comprises a pair of magnets disposed on the outer face of a pair of proximal teeth, the magnets being configured to send a signal to a receiving/transmitting unit upon the proximity between the magnets. The receiving/transmitting unit is configured to send information relating to the time and frequency of reception of the signals to an application in a mobile device.

Still for this configuration, the contact means configures a shape that covers the surface of at least a portion of one to four teeth by pressing the contact means against at least a portion of one to four teeth to which it is associated.

Moreover, in this configuration, the contact means comprises a thickness between 0.5 and 10.0 millimeters, 1.0 and 8.0 millimeters, 2.0 and 7.0 millimeters, or 2.0 and 4.5 millimeters. Optionally, the contacting means is at least partially constituted of a metal filament.

This invention also includes a second, alternative configuration for the intraoral device for generation of contact perception between teeth, the device being configured for application to the upper or lower dental arch of a user, comprising a contact means configured to be associated with at least a portion of the upper or lower dental arch, the contact means being at least partially constituted of a metal filament, the device being configured to generate a perception of contact to the user upon the contact between the contact means and at least a portion of the opposing arch to at least a portion of one to four posterior teeth.

In this configuration, the contact means comprises a shape that covers the surface of at least a portion of one to four teeth and is configured to adopt the shape of the surface of at least a portion of one to four teeth by pressing the contact means against at least a portion of one to four teeth to which it is associated.

Also, the contact means comprises a state of malleability and a state of stiffness in at least a portion of its extent. The contact means configures the malleability state when subjected to a softening temperature range.

Particularly, at least a portion of the contact means is configured to, in the malleability state, assume the surface shape of at least a portion of one to four teeth upon its deformation by pressing the contact means against at least a portion of one to four teeth to which it is associated.

Moreover, the contact means is a splint whose thickness is at most the distance between the upper and lower arches of the user in a resting position of the user's jaw and comprises a thickness between 0.5 and 10.0 millimeters.

Still in this configuration, the contact means alternatively comprises a thickness between 1.0 and 8.0 millimeters, 2.0 and 7.0 millimeters or 2.0 and 4.5 millimeters, and the contact means comprises a rigid surface and a moldable surface, the moldable surface comprising the state of stiffness and the state of malleability.

In this configuration, the contact means comprises, between the rigid surface and the moldable surface, a pressure sensor, the pressure sensor being connected to an application and being configured to send a signal to the application upon contact of the device with at least a portion of the opposing arch.

Moreover, the device comprises a pair of magnets disposed on the outer face of a pair of proximal teeth, the magnets being configured to send a signal to a receiving/transmitting unit upon the proximity between the magnets. Also, the receiving/transmitting unit is configured to send information relating to the time and frequency of reception of the signals to an application of a mobile device.

This invention further comprises a method of applying the intraoral device comprising the following steps:
  molding the contact means into a shape that accompanies the surface of at least a portion of one to four posterior teeth (D1) of the user's upper or lower arch; and
  attaching the contact means to at least a portion of one to four posterior teeth of the user's upper or lower arch.
  Particularly, the method further comprises the following steps:
  softening at least a portion of the contact means by heating it to a softening temperature range;
  pressing the contact means against a portion of one to four posterior teeth of the user's upper or lower arch;
  pressing the contact means against the portion of one to four posterior teeth of the user's upper or lower arch when at least a portion of the contact means is in the softening temperature range;
  hardening at least a softened portion of the contact means.

This invention further comprises a method for determining the thickness of the above-mentioned intraoral device, the method comprising the following steps:
  continuously sensing the load acting on the masticatory muscles of the user;
  gradually moving the user's jaw towards opening and/or closing;
  identifying the minimum load acting on the masticatory muscles of the user;
  measuring the distance between the user's upper and lower arches corresponding to the minimum load acting on the user's masticatory muscles; and
  determining the thickness of the device 10 according to the distance measured between the upper and the lower arches of the user corresponding to the minimum load acting on the user's masticatory muscles.
  Particularly, the method further comprises the steps of:
  continuously monitoring the distance between the user's upper and lower arches; and
  identifying the distance between the user's upper and lower arches corresponding to the minimum load acting on the user's masticatory muscles.
  emitting a sound and/or luminous signal whose frequency and/or intensity is determined by the load acting on the masticatory muscles of the user.

SUMMARIZED DESCRIPTION OF DRAWINGS

Figure 2:
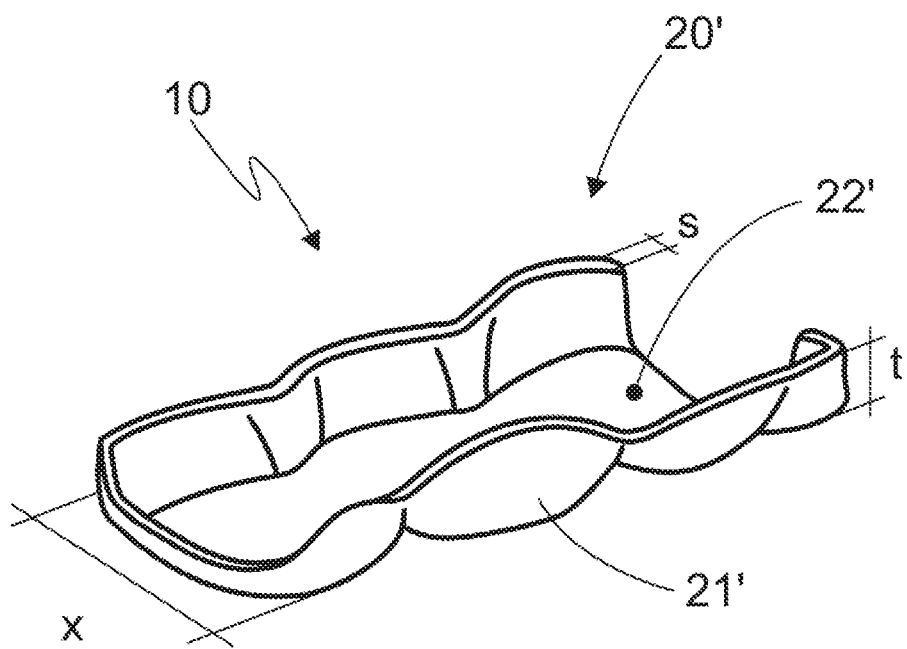
Figure 3A:
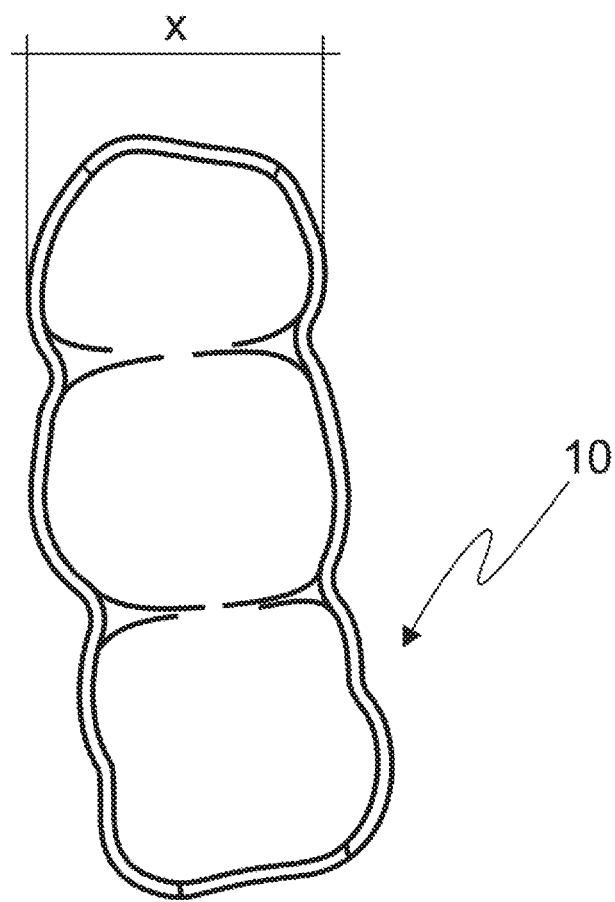
Figure 3B:
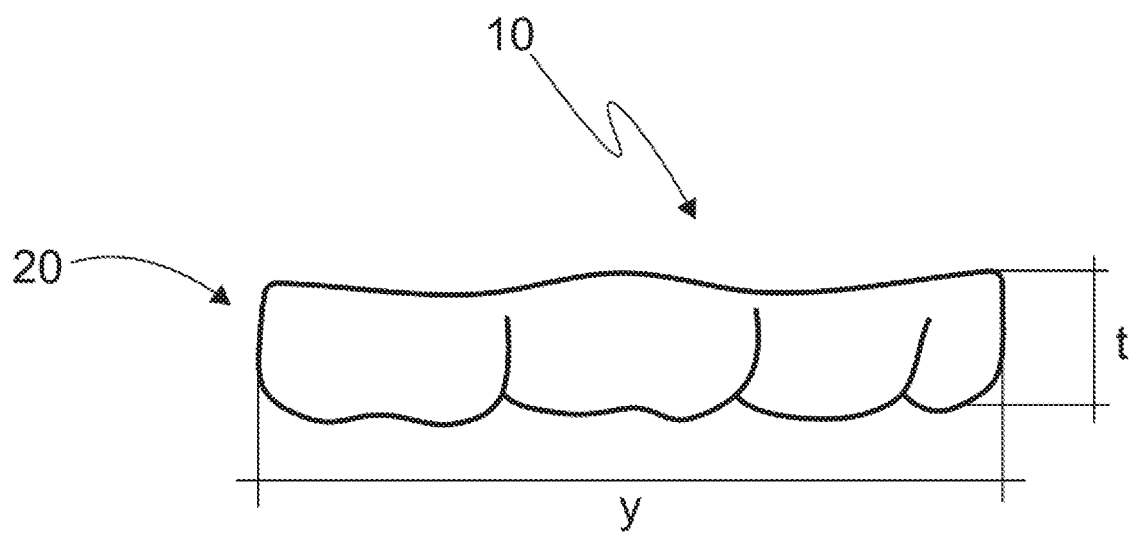
Figure 4:
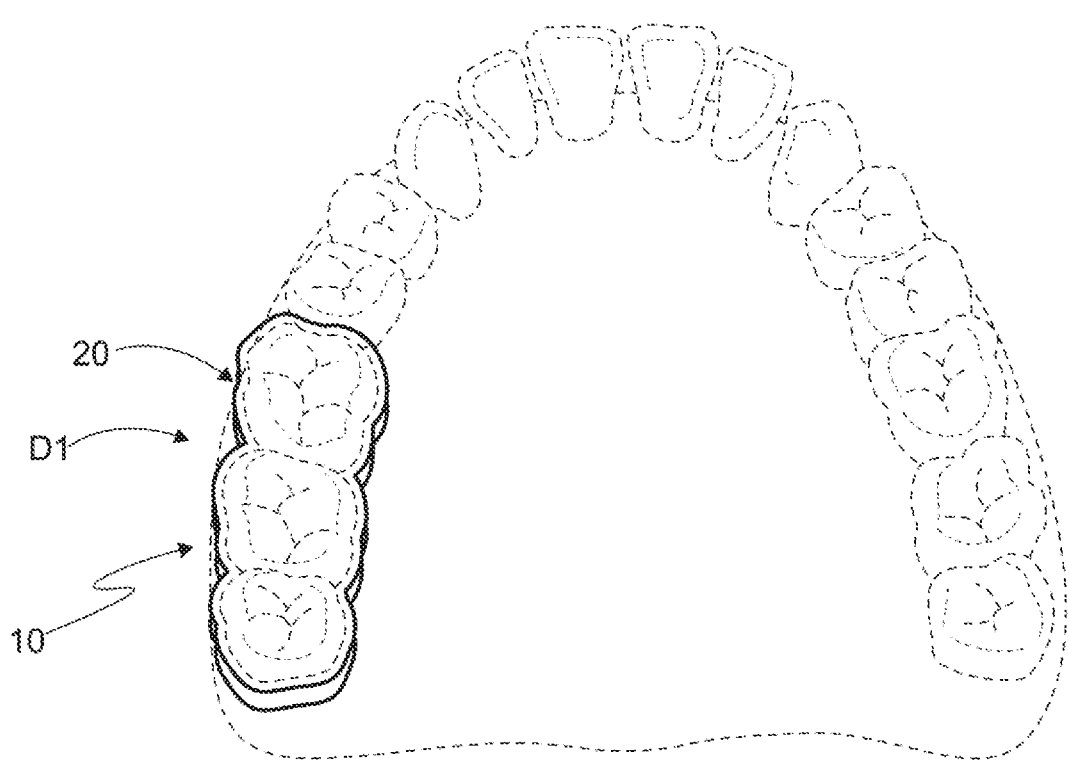
Figure 5B:
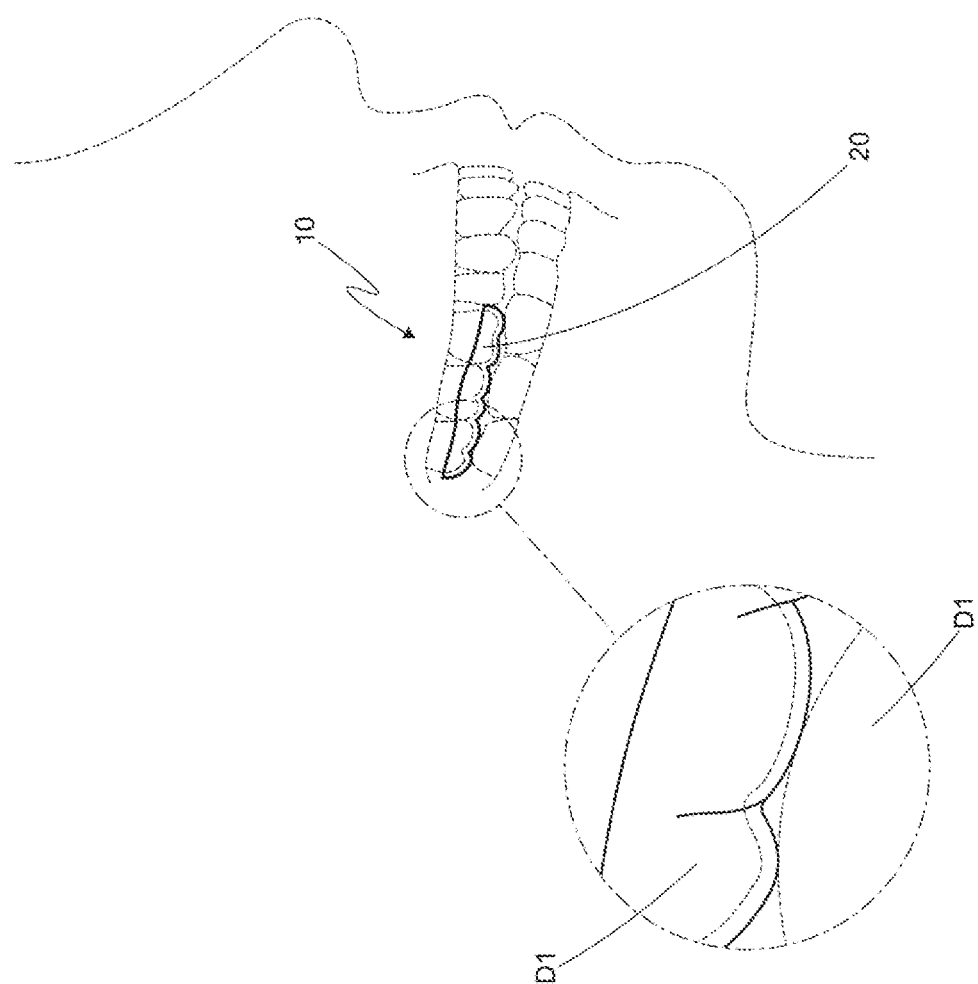
Figure 5A:
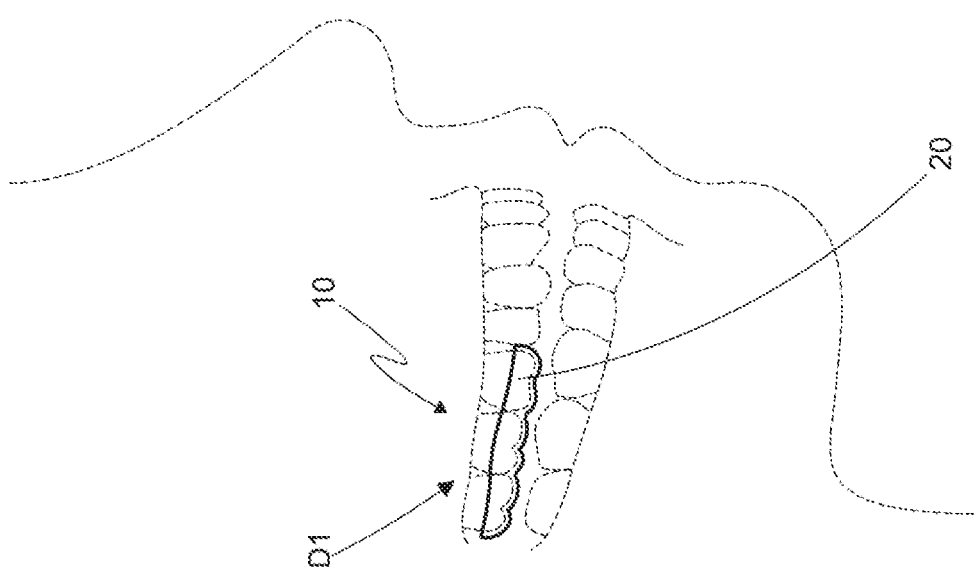
Figure 6:
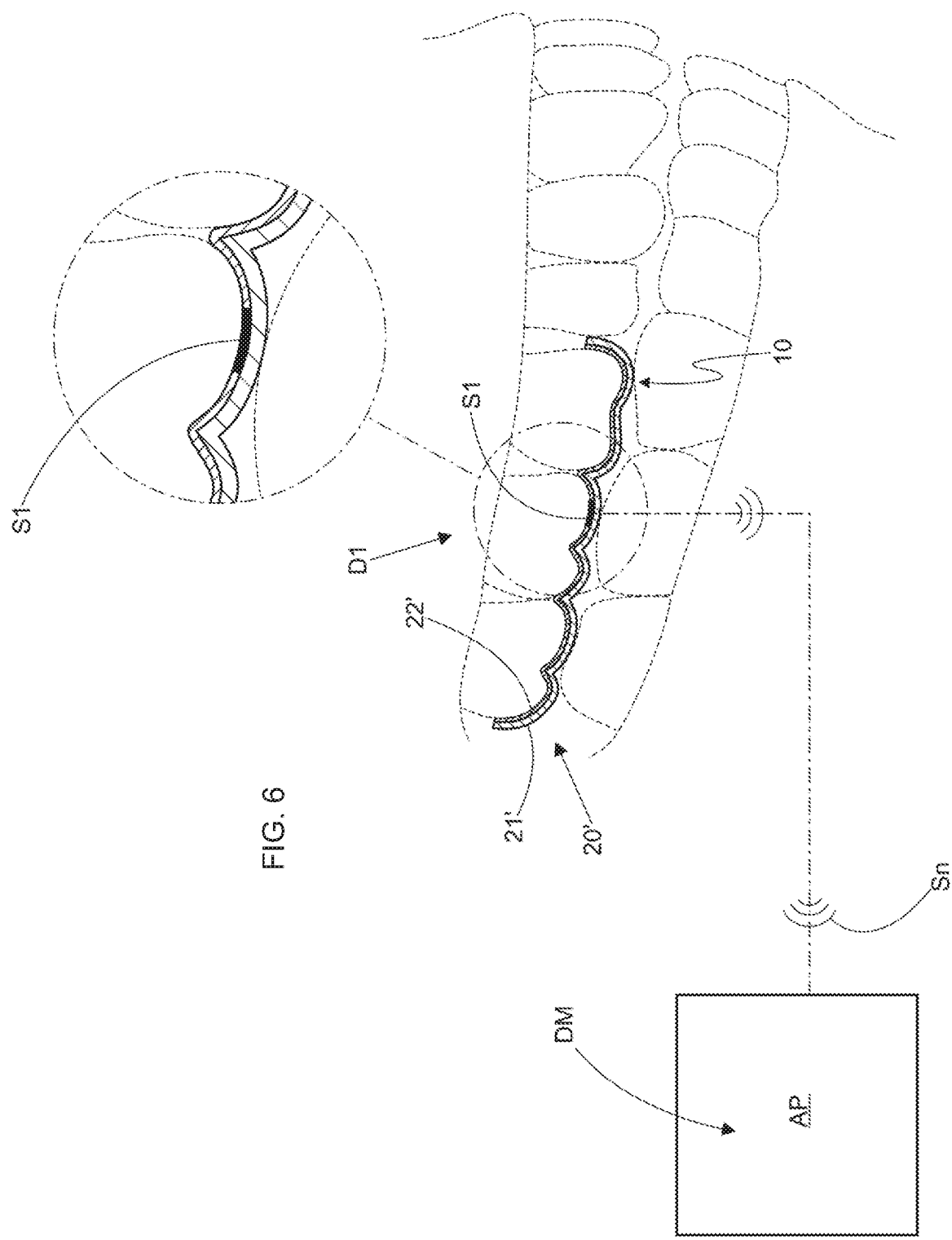
Figure 7:
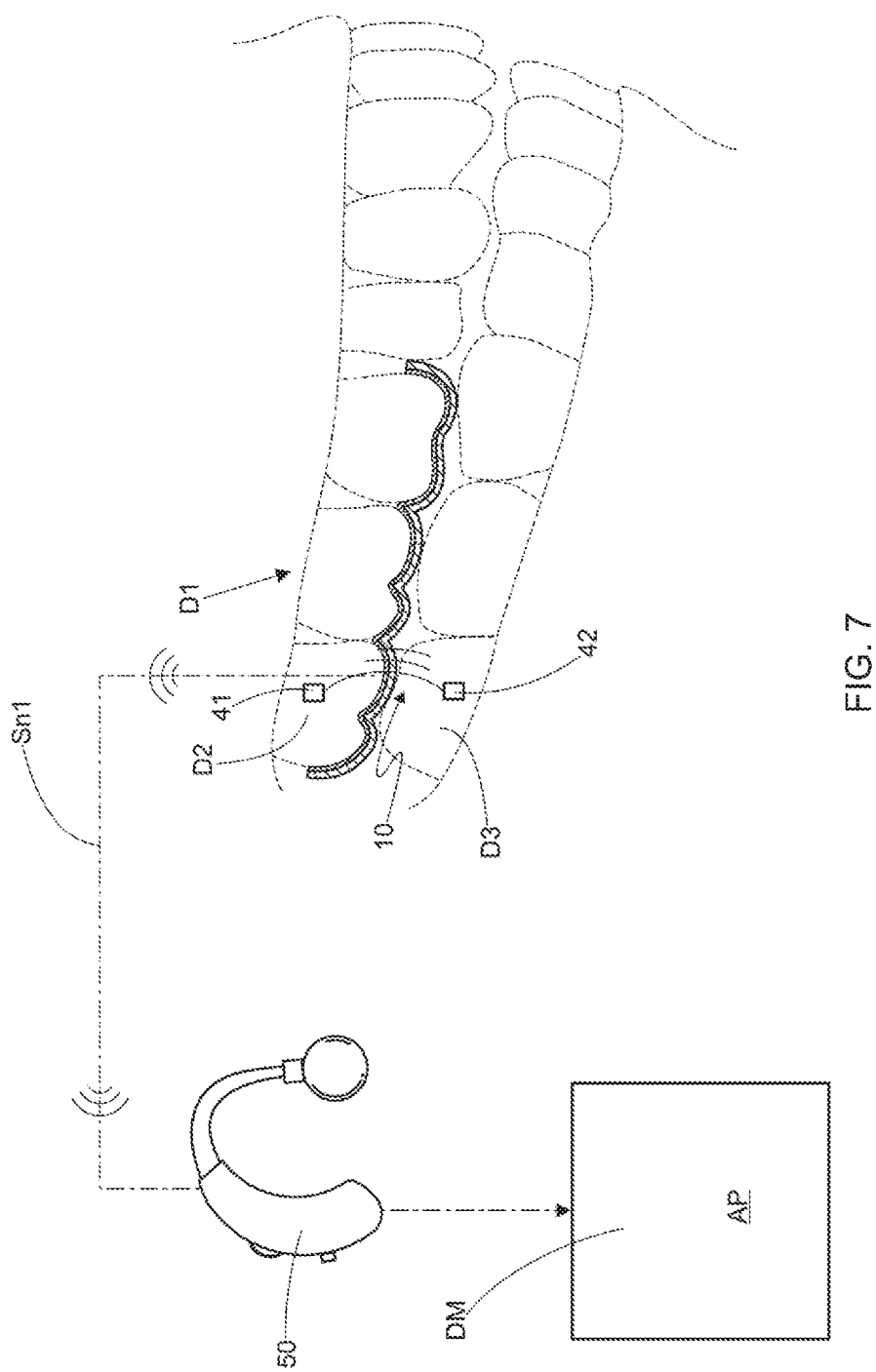
Figure 8A:
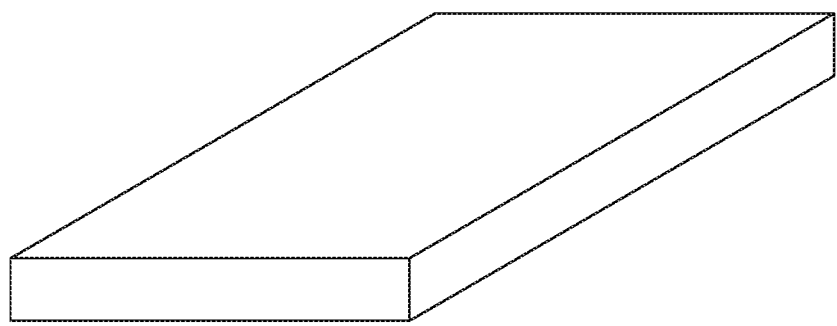
Figure 8B:
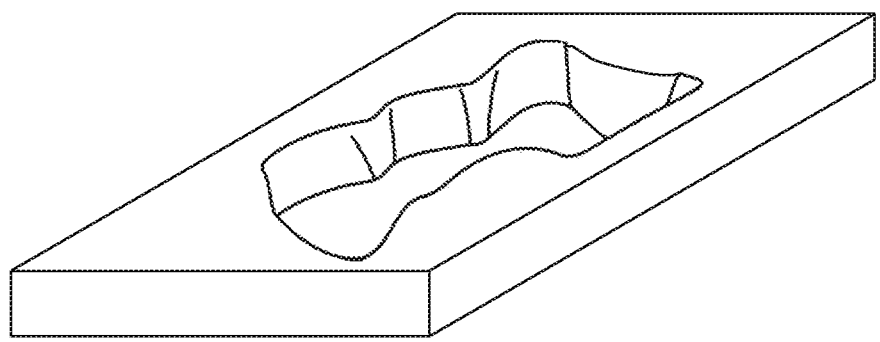
Figure 8C:
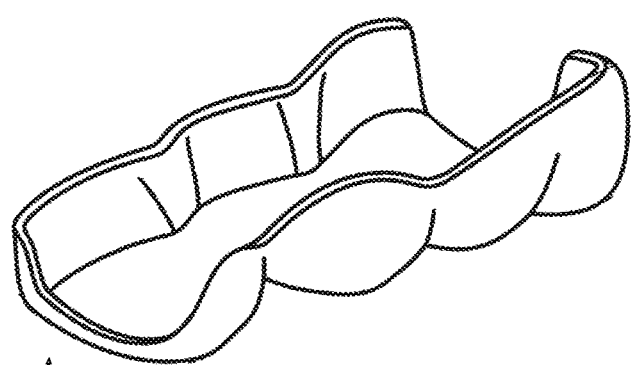
Figure 10A:
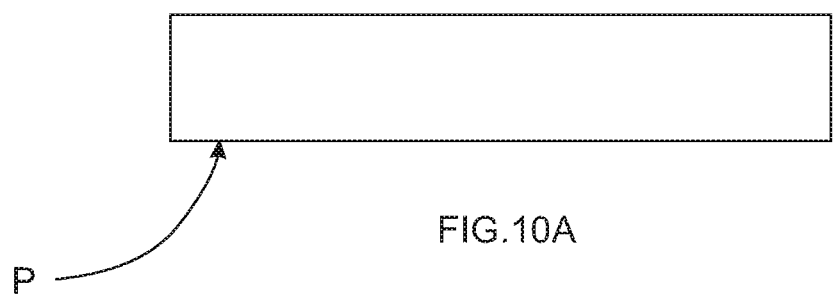
Figure 10C:
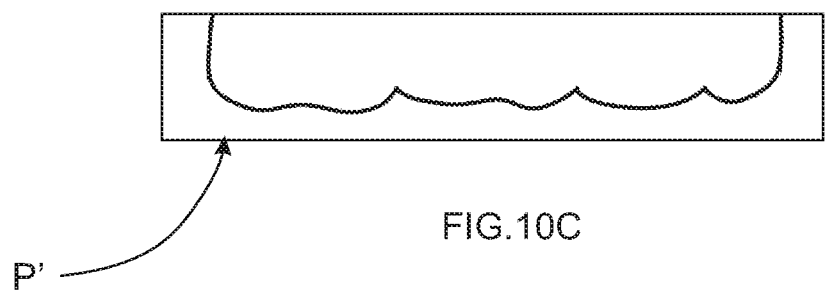
Figure 10C:
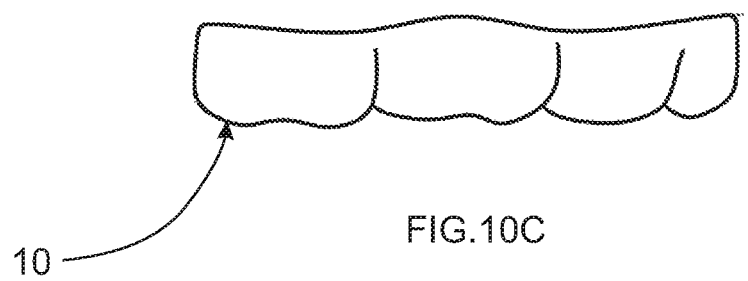

This invention will hereinafter be more fully described based on an example of operation shown in the drawings. The figures show:

FIG. 1—it is a perspective view of the intraoral device of this invention in its preferred configuration;

FIG. 2—it is a perspective view of the intraoral device of this invention in a first alternative configuration;

FIG. 3A—it is a top view of the intraoral device of this invention in its preferred configuration;

FIG. 3B—it is a side view of the intraoral device of this invention in its preferred configuration;

FIG. 4—it is a top view of a lower arch of a user with the device of this invention applied thereto;

FIG. 5A—it is a side view of the face of a user detailing the positioning of the intraoral device of this invention on the upper arch in a situation of no contact with an opposing tooth;

FIG. 5B—it is a side view of the face of a user detailing the positioning of the intraoral device of this invention on the upper arch in a situation of contact with an opposing tooth;

FIG. 6—it is a side view of the face of a user detailing the positioning of the intraoral device of this invention in a second preferred configuration, on the upper arch;

FIG. 7—it is a side view of the face of a user detailing the positioning of the intraoral device of this invention in a third preferred configuration, on the upper arch;

FIG. 8A—it is a perspective view of a molding plate to manufacture the device of this invention;

FIG. 8B—it is a perspective view of a molding plate to manufacture the device of this invention in the shape of the portion of the user's arch molded on its surface;

FIG. 8C—it is a perspective view of the device of this invention after having been obtained from the molding plate;

FIG. 9A—it is a top view of a molding plate to manufacture the device of this invention;

FIG. 9B—it is a top view of a molding plate to manufacture the device of this invention in the shape of the portion of the user's arch molded on its surface;

FIG. 9C—it is a top view of the device of this invention after having been obtained from the molding plate;

FIG. 10A—it is a side view of a molding plate to manufacture the device of this invention;

FIG. 10B—it is a side view of a molding plate to manufacture the device of this invention in the shape of the portion of the user's arch molded on its surface;

FIG. 10C—it is a side view of the device of this invention after having been obtained from the molding plate;

DETAILED DESCRIPTION OF THE FIGURES

It is first clarified that intraoral device 10 is designed for awake (daytime) treatment by generating a contact perception between the device and at least one opposing tooth in real time for the user's instant understanding and immediate control of parafunctions. In other words, the tightening of the jaw is immediately perceived and interrupted by the patient with the use of this device.

The intraoral device of this invention is configured to be applied to the upper or lower dental arch of a user, preferably at the rear of the arch, to be arranged in opposition to the other arch, i.e., opposite the opposing teeth. For a better understanding of this invention, the term "opposing tooth" is to be understood as any tooth on the arch opposite the arch to which the device of this invention is applied.

Essentially, intraoral device 10 of this invention comprises a contact means 20, 20' configured to be associated with at least a portion of one to four posterior teeth D1 of the user's upper or lower arch. Said device 10 is further configured to generate a perception of contact to the user upon the touch/contact of the contact means 20, 20' to an opposing tooth of the arch to which said device 10 is associated.

More specifically, the splints 20, 20' are designed to cover the occlusal and lateral surfaces of up to four posterior prosthetic teeth or crowns D1, as more fully seen in FIGS. 5A and 5B, and can be placed on both the right and left sides of the dental arch, either in the upper or lower arch.

The number of teeth covered by device 10 depends on the anatomy of each user's arch. During development studies of this invention, it has been determined that covering at most four teeth of the arch is the ideal situation for maintaining oral functionality (such as speech, salivation ability, among others) and patient aesthetics, as well as to maintain the perception of a slight but efficient contact as perceived by the user.

In addition, a portion of one to four overlapping teeth allows to avoid a very large load on a single area of the arch, such as, for example, an area comprising a prosthesis which is, of course, more fragile than an actual tooth, thus preventing its breakage.

In particular, to ensure a comfortable and efficient use of this invention, the contact means 20, 20' has a thickness that is less than the distance between the upper and lower arches of the user in a situation of lower load on the jaw (more specifically, on the masticatory muscles) of the user. This situation of lower load corresponds to the resting state of the jaw, that is, its natural position when not being actively used. It is understood, therefore, that the occurrence of parafunctions depends on the closure of the jaw beyond this resting state, which requires the use of device 10 of this invention.

Thus, device 10 is configured so that the thickness of the contact means 20, 20' is less than the distance of the arch at rest, so that the user has the perception of contact only in case a parafunction occurs.

In a preferred configuration, and as can be seen in FIG. 1, said intraoral device 10 comprises a splint 20. Such splint 20 may be integrally or partially composed by a number of different materials, such as acrylic resin, thermoplastic material, metal, silicone or any other biocompatible material.

Particularly, to ensure a better fit and to make the use of device 10 comfortable to the user, the contact means 20, 20' comprises a shape that covers the surface of at least a portion of the teeth D1 to which device 10 is associated. This feature of a shape that covers the portion of the teeth D1 allows an accurate fit of device 10 on the user's arch, ensuring a comfortable use thereof. FIG. 4 shows a top view of the arch of a user with device 10 associated with a portion of teeth D1.

To obtain such a shape, the contact means 20, 20' of device 10 may, in particular, be molded into the shape of the user's arch surface in a variety of ways. It is possible, for example, to mold the contact means 20, 20' by using a replica of the user's arch in the laboratory. It is also possible to have a dental professional mold the contact means 20, 20' directly in the patient's mouth.

Notwithstanding the foregoing, a material of particular relevance for the construction of splint 20 in this preferred configuration of device 10 is thermoplastic material, which comprises a state of rigidity and a state of malleability, wherein the malleability state is configured when the material is subjected to a softening temperature range.

Thermoplastic materials are widely known by the state of the art, and it is also known that the softening temperature range changes drastically between one material and another. Therefore, further details of this material will not be explored in this application, it being understood only that a thermoplastic material whose softening temperature is bearable to the user upon insertion of device 10 inside their mouth within said gap is applicable.

In this sense, device 10 may have its contact means 20, 20' made of thermoplastic material, which can be easily handled and shaped by the manipulation of its temperature. Although a dental practitioner may assist the user in this molding, this invention allows the user to perform the molding of the splint for it to fit in their arch, by using the construction and the arrangement of device 10 and the material in its constitution.

More specifically, the molding of the contact means 20, 20' into the shape of the user's arch surface can be particularly accomplished by pressing the contact means 20, 20' against the portion of the rear teeth D1 chosen. Thus, the contact means 20, 20' takes the shape of the surface of the desired portion of the arch, configuring an efficient fit.

This molding method can be used for materials with a malleable state and a rigid state, such as acrylic resin and thermoplastic materials. For thermoplastic materials, and in accordance with what this invention proposes, the user him or herself can perform the molding and application in an intuitive and practical manner.

In this sense, the user can purchase a P splint of thermoplastic material (easily distributed material that can be supplied in suitable establishments such as pharmacies), whose temperature range is intended for this use. A representation of this splint is illustrated in FIGS. 8A, 9A and 10A, noting that such representation is merely intended to exemplify the construction and use of the splint, such representation not being a mandatory way for achieving the objects of this invention.

The heating of the material can be done in any available way, such as dipping in hot water. After reaching the softening temperature range of the thermoplastic material, splint P can then be inserted into the mouth by the user, and the molding is accomplished by pressing splint P against the portion of one to four teeth D1 by the user him or herself. FIGS. 8B, 9B and 10B illustrate the state of splint P after it has been pressed against said portion.

The pressing can be carried out by manually pushing splint P against the teeth D1, or if the user bites the splint after it has been positioned adjacent to the teeth, or by any other suitable means. Thus, splint P takes the shape of the surface of the arch. Finally, splint P is hardened, usually by cooling the thermoplastic material, and the edges of splint P are adjusted by cutting and sanding, for greater user comfort, thus obtaining the final shape of device 10. FIGS. 8C, 9C and 10C illustrate device 10 obtained after the adjustment stage.

Again, these procedures for applying device 10 of this invention may be performed by the user without the help of a dental practitioner or any other person, although the intervention of the practitioner per se is not an impediment to the application of the procedure.

It is further emphasized that the contact means 20, 20' (particularly a splint 20, 20') may have only a portion of its structure consisting of thermoplastic material. Such a construction is desirable mainly in cases where the molding is performed through a user bite, so that the opposing arch does not interfere with the modeling of the chosen arch, i.e. so that the contact means 20, 20' is not pressed by the opposing arch and takes the shape thereof.

An alternative configuration of device 10 of this invention, shown in FIG. 2, and in more detail in FIGS. 6 and 7, comprises only a portion of the contact means 20' made of thermoplastic material. More specifically, the contact means 20' comprises a rigid surface 21' and a moldable surface 22' opposite each other.

The rigid surface may be a rigid material or a material that has a state of permanent stiffness after molding, such as acrylic resin. The moldable surface comprises a state of stiffness and a state of malleability, the state of malleability being particularly configured through a softening temperature, for example using thermoplastic material.

As in the case of the above-mentioned preferred configuration, the contact means 20' in its first alternative configuration is associated with a portion of one to four rear teeth D1 of the user's upper or lower arch, taking the shape of the surface of this portion. However, in this first alternative configuration, the molding of the contact means 20' is done by pressing the moldable surface 22' against the portion of the teeth D1.

The presence of the rigid portion 21' on the surface opposite the arch to which device 10 is applied prevents the user's bite (or any other means used to press the contact means 20') from altering the shape of this surface, thereby allowing the obtainment of a contact means 20' whose surface that will touch the opposing tooth is not impaired by the opposing arch, allowing a more practical application and a better contact perception of the final product.

It should also be noted that the rigid surface 22' may be removable or permanent, i.e. it may serve only as a tool to prevent the deformation of the surface of device 10 or also as an integral part of the contact portion with the opposing tooth. In the case of a permanent rigid surface 22', it may be pre-molded into a suitable contact shape, such as a uniform surface or the surface shape of the portion of one to four teeth D1 chosen for the application of device 10.

FIG. 6 shows a second alternative configuration of the device of this invention. In this configuration, device 10 comprises a contact means 20' made up of a rigid surface 21' and a moldable surface 22', like the first alternative configuration shown in FIG. 2.

In addition, this second alternative configuration receives, between the rigid surface 21' and the moldable surface 22', a pressure sensor S1 connected to an application AP installed on mobile devices DM, the mobile device being either a smartphone, a tablet or another device. Pressure sensor S1 is configured to detect the generation of contact perception to the user upon the touching of device 10 on any opposing tooth and sends information to the application AP via a wireless signal Sn. In this way, each time the opposing tooth touches the plate 20', the sensor S1 will emit a signal Sn which will be captured by the application AP.

In this second preferred configuration, the application AP has the function of mapping all the daily contacts that can cause the aforementioned disorders and helping a dental professional as well as the patient him or herself to reduce those habits.

This application AP also allows the patient to manually enter, through the data collected by the sensor, the time, intensity, frequency, pattern and location of the discomfort or pain, thus enabling, through this monitoring, a more accurate diagnosis and treatment of these dysfunctions.

FIG. 7 shows a third alternative configuration of the device of this invention. The device comprises a contact means 20, 20' (splint) placed on the user's arch as seen in the other configurations. Additionally, device 10 comprises a pair of magnets 41, 42 each installed on the outer surface of a pair of proximal teeth D2, D3, i.e., close to the region where device 10 will be applied.

Said magnets 41, 42, when brought together by the tightening between the upper and lower arches, create a magnetic field which emits a signal Sn1 to a receiving/transmitting unit 50 which may be positioned in a location external to the mouth, for example, behind the ear.

Thus, when the patient contracts their muscles, the Sn1 signals are picked up by the unit 50 which transmits this information to the application AP, installed on mobile devices DM and mapping all the daily contacts and at what time and frequency they occur.

Device 10 of this invention further comprises a fourth alternate configuration, wherein the contact means 20, 20' comprises a structure, at least partially, preferably consisting of metal filaments. As for the splints in the other configurations, the structure is disposed on at least a portion of up to four rear teeth D1 of the upper or lower dental arch and is configured to be fitted on the enamel of tooth D1 and to adopt the anatomical shape of the portion of the teeth D1. Such a structure can be used to promote a better fitting of the contact means 20, 20' to the portion of the teeth D1 by means of metal projections configured to fit on the sides of the teeth.

In any of the above configurations, preferably, and as best identified in FIGS. 1 to 3B, the contact means 20, 20' are sized with a thickness "s" between 0.5 and 10.0 mm; a width "x" between 6 and 10 mm; a height "t" between 3 and 5 mm; and a length "y" between 10 and 40 mm.

In particular, the thickness "s" of the contact means comprises specific intervals covering different thicknesses of device 10 for application in or by different users, as each gap considers a range of specific distances between the user's upper and lower arches. These ranges will be explored in detail further on.

More specifically, a user understands a jaw positioning state in which there is a minimum load on their masticatory muscles. This state, hereafter referred to as the "resting state of the jaw", represents the positioning of the jaw (and hence the upper and lower arches) when it is not actively being used, which accounts for most of the state of the jaw during the waking period. Of course, any unconscious movement of the jaw during its resting state reflects a parafunction that must be corrected.

For the detection of parafunctions by device 10 of the present invention to be as efficient as possible, the thickness of the contact means 20, 20' should be determined according to the distance between the upper and lower arches during the resting state of the jaw. Briefly, the thickness of the contact means 20, 20' should be slightly less than said distance, so that it does not produce the contact perception during this resting state but can produce such perception upon the slightest indication of occurrence of parafunction.

In this way, the device of this invention comprises several thickness ranges for various possible distances between the arches of a user.

It is emphasized that in any of the aforesaid configurations, device 10 allows the perception of contact between device 10 and at least a portion of the opposing arch to the arch to which device 10 is applied, allowing the user to identify the unconscious approach of the arches and, consequently, the occurrence of a parafunction. Having the knowledge of the approximation of the teeth, the user moves them to a position such as that of FIG. 5A, where there is no perception of contact, and is continuously made aware to avoid the occurrence of bruxism-related parafunctions.

It should also be noted that the device of this invention does not impair the normal oral functionalities of the user, and does not influence the aesthetics of their mouth, thanks to its small size and arrangement.

Considering the foregoing, it becomes clear that the device of this invention promotes the perception of contact between said device and the opposing teeth of the opposing arch, assisting the user in detecting and correcting the parafunctions leading to the various temporomandibular disorders.

At the same time, the device of this invention allows this correction of the parafunctions in a manner that does not impair the user's mouth functions, and it also maintains the aesthetic of the mouth intact. The reduced size and the specific arrangement of the device also allow practicality in its use, as well as ease of manufacture and reduced cost of the device.

It should be noted that, during the use of the device, dental contact that occurs during swallowing of the patient's saliva should be considered functional, and that during this act, if the individual has the device in position, the contact on the splint is considered normal. In this sense, any other contact can be considered parafunctional, and these are the contacts that must be controlled and reversed.

Studies performed by the application of device 10 of this invention on users have given some feedback about applications that exceed expectations related only to bruxism and correlates. These are:

The use of the intraoral device of this invention allows the reduction of TMJ inflammation and orofacial and cervical myalgias caused by constant muscle contraction which, consequently, lead to fatigue in musculature and joint disorders as well as inflammation in the soft tissues adjacent to TMJ, local swelling and compression of the internal ear artery. The decrease in this inflammation can control the presence of possible ringing in the ears. In fact, local swelling caused by inflammation of the TMJ, such as capsulitis, for example, could press noble structures of the inner ear, such as the artery and nerve endings of this organ and lead to a secondary auditory disorder, such as tinnitus.

The decrease in muscle contraction obtained by the biofeedback treatment of real-time immediate perception of involuntary contractions by use of the device of this invention allows for facial relaxation and consequent reduction of expression lines, commonly known as the nose to mouth wrinkles (nasolabial folds);

The dental application of the device in question reeducates and controls the movements of involuntary contractions, allowing the substantial reduction of functional and aesthetic problems such as reduction of crown and prosthesis breakdown, pathological tooth movement, dental wear, cervical lesions (loss of enamel in the cervical region), periodontal problems associated with mechanical stress;

The device of this invention promotes aid in the treatment of periodontal problems by reducing the mechanical load between the dental arches though the use of the innovative intraoral device, reducing tooth loss;

The use of the intraoral device of this invention promotes the obligatory spacing between the dental arches, helping the patient to maintain their Free Functional Space, preventing onychophagia, that is, nail biting, since for this it is necessary to have pressure between the arches; when the user is using the device, this is therefore prevented; and The use of the intraoral device of this invention decreases the patient's state of permanent and chronic pain in the regions and organs mentioned above, it also acts in the Central Nervous System decreasing its sensitization, thus attenuating the perception of other existing pains.

In order to prove the effectiveness of this invention, the results of clinical trials performed with users of this device, each presenting different symptoms related to temporomandibular disorders, are presented below, with a return to evaluate the improvement scheduled for 7, 30 and 90 days after the beginning of the treatment:

| User 1 | |
|---|---|
| Symptoms | Headaches for more than 10 years |
| Beginning of the Treatment | Aug. 13, 2016 |
| Level of pain before the treatment (0 to 10) | Level 8 |
| $1^{st}$ Return (7 days) | Level of improvement of the main complaint: 8 (from 0 to 10). The user informed that they felt more tightening between 11am and 2pm. |
| $2^{nd}$ Return (30 days) | Level of use of the device of this invention: almost every day. Patient assessment: They did not have any more headaches. Level of improvement of the main complaint (from 0 to 10): 10 (ten). |
| $3^{rd}$ Return (90 days) | Level of use of the device of this invention: almost every day. Patient assessment: They did not have any more headaches. Level of improvement of the main complaint (from 0 to 10): 10 (ten). |

| User 2 | |
|---|---|
| Symptoms | Ringing in the ear and severe headaches for more than 5 years. |
| Beginning of the Treatment | Aug. 13, 2016 |
| Level of pain before the treatment (0 to 10) | Level 7 |
| $1^{st}$ Return (7 days) | Evaluation of supposed improvement. |
| $2^{nd}$ Return (30 days) | Level of use of the device of this invention: every day. Patient assessment: There were no more ringing in the ear or headaches. Level of improvement of the main complaint (from 0 to 10): 9 (nine). |
| $3^{rd}$ Return (90 days) | Level of use: almost every day. Patient assessment: Did not have any ringing in the ear or headaches. Level of improvement of the main complaint (from 0 to 10): 10 (ten). |

| User 3 | |
|---|---|
| Symptoms | Bruxism, muscle tension and headaches. |
| Beginning of the Treatment | Aug. 20, 2016 |
| Level of pain before the treatment (0 to 10) | Level 9 |
| $1^{st}$ Return (7 days) | Evaluation of improvement: there was greater perception of the tightening. The user recognizes a "retraining of the brain" to "move away the teeth". |
| $2^{nd}$ Return (30 days) | Level of use in 30 days: 20 days. Patient assessment: There were no more ringing in the ear or headaches. Level of improvement after treatment (from 0 to 10): 10 (ten). |
| $3^{rd}$ Return (90 days) | Level of use: almost every day. Patient assessment: Did not have any ringing in the ear or headaches. |

-continued

User 3

Level of improvement after treatment (from 0 to 10): 10 (ten).

The results above show that this invention is effective in treating different temporomandibular disorders, and FIG. 8 shows a graph summarizing the statistical results of the tests performed.

Additionally, this invention comprises a method for applying an intraoral device 10 as described above, which comprises essentially the following steps:
molding the contact means 20, 20' into a shape that covers the surface of at least a portion of one to four posterior teeth D1 of the user's upper or lower arch; and
attaching the contact means to at least a portion of one to four posterior teeth D1 of the user's upper or lower arch.

For devices 10 consisting at least partly of a thermoplastic material, the method of application further comprises the following step:
softening at least a portion of the contact means by heating it to a softening temperature range.

For devices 10 incorporating the use of material having a rigid state and a malleable state, the method of application further comprises the following step:
pressing the contact means 20, 20' against a portion of one to four posterior teeth D1 of the user's upper or lower arch.

If the malleable state results from the heating of the contact means 20, 20', the method further comprises the following step:
pressing the contact means 20, 20' against the portion of one to four posterior teeth D1 of the user's upper or lower arch when at least a portion of the contact means 20, 20' is in the softening temperature range.

And for materials with rigid and malleable states, the method of application further comprises the following step:
hardening at least a softened portion of the contact means 20, 20'.

Moreover, as previously described, for the detection of parafunctions by device 10 of the present invention to be as efficient as possible, the thickness of the contact means 20, 20' should be determined according to the distance between the upper and lower arches during the resting state of the jaw.

In accordance with this need, this invention further comprises a method of determining the thickness of an intraoral device such as the aforesaid, which essentially comprises the steps of:
Continuously monitoring the load acting on the user's masticatory muscles;

This first stage comprises obtaining information, in real time, relative to the load acting on the user's masticatory muscles, preferably by means of sensors. The monitoring of the load can be performed through procedures such as electromyography or electromyography, or any other procedure that allows for the monitoring of the loads acting on the masticatory muscles in real time.

In the case of electromyography, which is the preferred procedure, the user has electrodes placed on the surface of the temporal and masseter muscles. The electrical impulses emitted by the muscles are captured by the electrodes and sent to a computer, which interprets and displays the images on a screen or similar.

Next, there is the stage of:
gradually moving the user's jaw towards opening and/or closing.

At this stage, the user is asked to open and/or close their jaw gradually. By maintaining the monitoring of the load acting on the masticatory muscles, we will obtain information about the intensity of the load acting on each position of the user's jaw.

After that, there is the next step:
identifying the minimum load acting on the masticatory muscles of the user.

Once the load information is obtained for each position of the user's jaw, it is identified at which point the acting load is minimum. This point corresponds to the aforementioned "resting state of the jaw," which corresponds to the state in which the user maintains their jaw during most of the waking period.

Once the minimum working load point has been identified, the following step is followed:
measuring the distance between the user's upper and lower arches corresponding to the minimum load acting on the user's masticatory muscles.

Once the minimum working load point is identified, the user returns to the aperture corresponding to this point, and then measures the distance between its corresponding upper and lower arches of this specific aperture. This distance will then correspond to the "resting distance" of the jaw, in which the user remains during most of their waking period. The resting distance between the upper and lower arches of a user is commonly in the range of 0.5 to 10.0 millimeters, particularly being between 1.0 and 8.0 millimeters, and even more particularly between 2.0 to 7.0 mm or even 2.0 to 4.5 mm.

The measurement of the distance be performed, for example, by a millimeter compass (commonly referred to as "Sprung Divider" or by the introduction of a mass of silicone between the user's arches at the point of resting distance thereof. The silicone mass adopts a thickness of the same value of the resting distance and, after its solidification, said thickness is measured.

Finally, we move on to the next step:
determining the thickness of device 10 according to the distance measured between the upper and the lower arches of the user corresponding to the minimum load acting on the user's masticatory muscles.

Having the resting distance of the jaw, the thickness of device 10 is determined according to this distance. In general, the thickness of device 10 will have a value slightly less than the value of the resting distance of the user's jaw, to prevent the perception of contact from occurring in the resting state of the jaw, while allowing consistent contact of device 10 to the opposing arch during the occurrence of parafunctions. However, the value of the thickness may be at most the value of the measured resting distance, so that the resting position of the user's jaw is not compromised.

Having described an example of preferred configuration, it should be understood that the scope of this invention encompasses other possible variations, being limited only by the content of the appended claims, including possible equivalents thereto.

The invention claimed is:

1. A device configured to be applied as a splint to an upper or lower dental arch of a user, covering at least a portion of one to four posterior teeth, the device having a thickness less than a distance between the user's upper and lower dental arches when a jaw of the user is in a resting state, and wherein the thickness is at least of a width to cause contact against the upper and lower dental arches perceptible to the user upon tightening of the user's jaw.

2. The device of claim 1, configured to assume a surface shape of at least a portion of one to four opposing teeth with which it is associated.

3. The device of claim 1, comprising a portion having a state of malleability and a portion having a state of rigidity.

4. The device of claim 3, characterized in that the malleability state is achieved when the device is subjected to a softening temperature range.

5. The device of claim 4, characterized in that at least a portion of the device comprising a contact means, when in the malleability state, assumes a surface shape of at least a portion of one to four opposing teeth upon its deformation by pressing the contact means against at least a portion of the one to four opposing teeth to with which it is associated.

6. The device of claim 1, comprising a thickness between 0.5 and 10.0 millimeters.

7. The device of claim 1, comprising a thickness between 1.0 and 8.0 millimeters.

8. The device of claim 1, comprising a thickness between 2.0 and 7.0 millimeters.

9. The device of claim 1, comprising a thickness between 2.0 and 4.5 millimeters.

10. The device of claim 1, comprising at least partially a metallic filament.

11. The device of claim 1, comprising a rigid surface and a moldable surface, the moldable surface comprising a state of rigidity and a state of malleability.

12. The device of claim 11, characterized in that the rigid surface is removable.

13. The device of claim 11, comprising between the rigid surface and the moldable surface, a pressure sensor, wherein the pressure sensor is configured to send a signal to an application of a mobile device upon a contact of the upper and lower arches, and wherein the application is configured to record upper and lower arch contacts.

14. The device of claim 1, further comprising a pair of magnets disposed on an outer face of a pair of proximal teeth such that the magnets are brought together upon tightening of the user's jaw, the magnets being configured to send a signal to a receiving/transmitting unit upon approximation between the magnets.

15. The device of claim 13, characterized in that the receiving/transmitting unit is configured to send information relating to a time and frequency of reception of the signal to an application of a mobile device.

16. A method to determine a thickness to make a device applied as a splint to an upper or lower dental arch, the method comprising steps of:
continuously monitoring a load acting on masticatory muscles of the user;
gradually moving the user's jaw towards opening and/or closing;
identifying a minimum load acting on the masticatory muscles of the user;
measuring a distance between the user's upper and lower arches corresponding to the minimum load acting on the user's masticatory muscles; and
determining the thickness to make the device according to the distance measured between the upper and the lower arches of the user corresponding to the minimum load acting on the user's masticatory muscles.

17. The method of claim 16, further comprising steps of:
continuously monitoring the distance between the user's upper and lower arches; and
identifying the distance between the user's upper and lower arches corresponding to the minimum load acting on the user's masticatory muscles.

18. The method of claim 16, further comprising emitting a sound and/or luminous signal whose frequency and/or intensity is determined by the load acting on the masticatory muscles of the user.

* * * * *